United States Patent
Rowland et al.

[11] Patent Number: 5,099,836
[45] Date of Patent: Mar. 31, 1992

[54] INTERMITTENT OXYGEN DELIVERY SYSTEM AND CANNULA

[75] Inventors: Robert O. Rowland, Hemet; Thomas C. Loescher, Encinitas, both of Calif.

[73] Assignee: Hudson Respiratory Care Inc., Temecula, Calif.

[21] Appl. No.: 467,308

[22] Filed: Jan. 17, 1990

Related U.S. Application Data

[63] Continuation of Ser. No. 104,771, Oct. 5, 1987, abandoned.

[51] Int. Cl.5 .................................... A61M 16/00
[52] U.S. Cl. ..................... 128/204.23; 128/204.26; 128/207.18
[58] Field of Search ............. 128/204.18, 204.21, 128/204.22, 204.23, 204.26, 206.18, 207.13, 207.18

[56] References Cited

U.S. PATENT DOCUMENTS

| | | | |
|---|---|---|---|
| 3,611,178 | 10/1971 | McConnell | 128/204.23 |
| 3,831,596 | 8/1974 | Cavallo | 128/204.23 |
| 4,054,133 | 10/1977 | Myers | 128/207.18 |
| 4,393,869 | 7/1983 | Boyarsky et al. | 128/204.23 |
| 4,519,387 | 5/1985 | Durkan et al. | 128/204.23 |
| 4,567,888 | 2/1986 | Robert et al. | 128/204.21 |
| 4,648,395 | 3/1987 | Sato et al. | 128/204.23 |
| 4,686,975 | 8/1987 | Naimon et al. | 128/204.23 |

Primary Examiner—Lee S. Cohen
Assistant Examiner—J. P. Lacyk
Attorney, Agent, or Firm—Jerry R. Seiler

[57] ABSTRACT

An improved system for delivering oxygen on demand to a user comprises a pressure transducer for sensing pressures during the breathing cycle of a user and for creating an electrical signal proportional to said sensed pressures, an electronic amplifier for amplifying the signal to at least 10,000 times the original signal strength, electronic filters for regulating the amplitude of the signal and for correcting the point of the signal where expiration stops and inspiration begins to correspond to zero respiratory pressure, an on/off switching circuit and cooperating valve drive circuit for switching to an on condition in response to a preselected first pressure and to an off condition in response to a preselected second pressure, and a valve driven by the valve drive circuit means for directing oxygen from an oxygen source to a user.

2 Claims, 5 Drawing Sheets

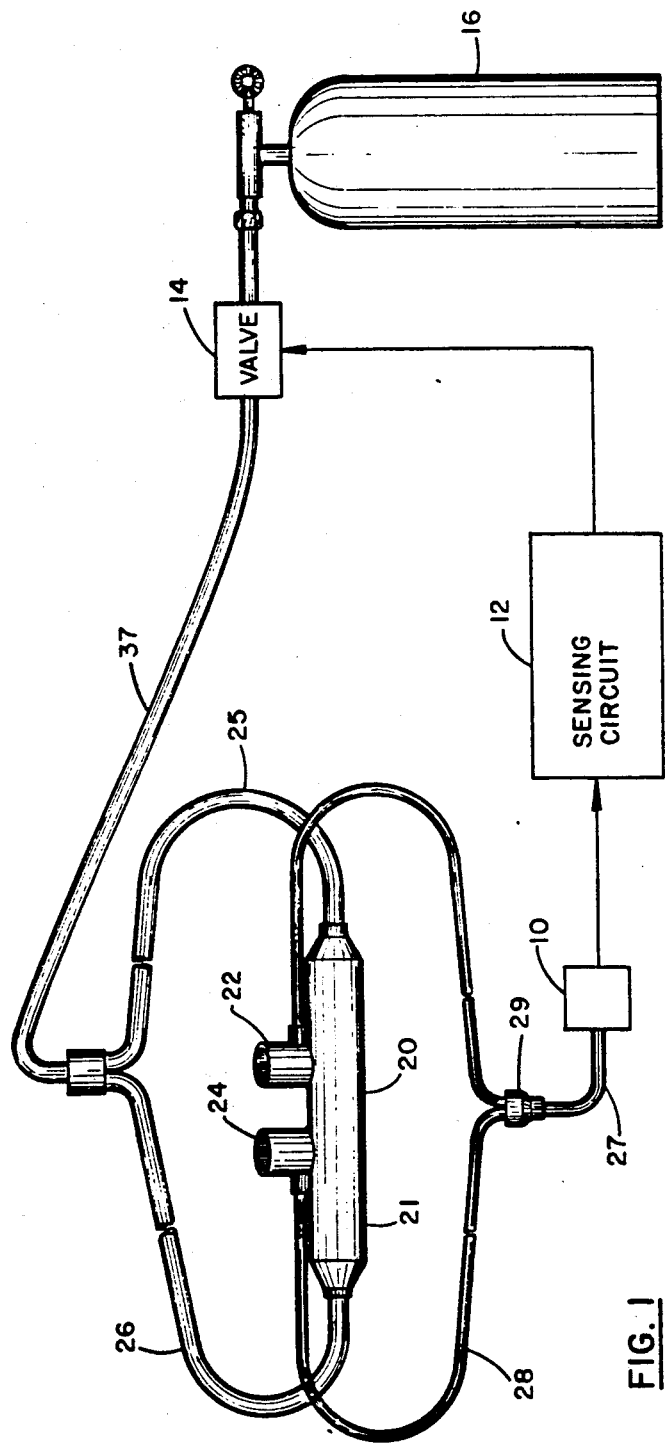
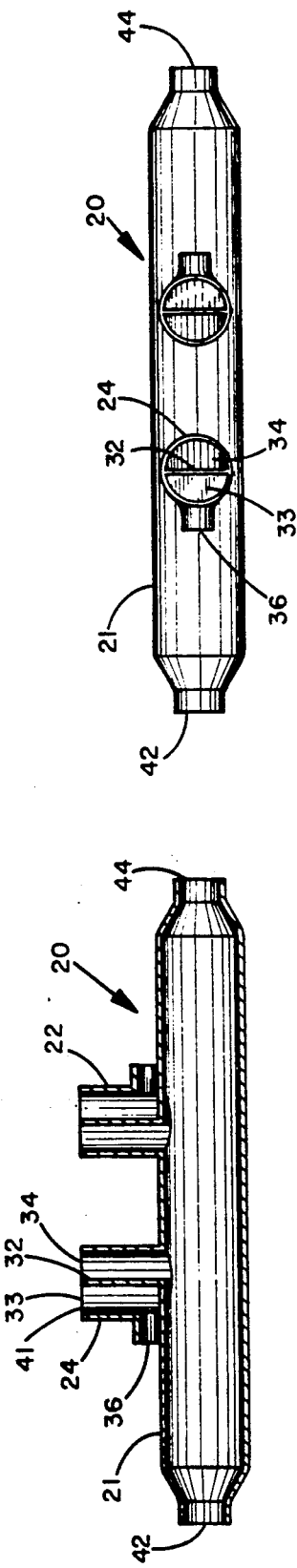
FIG. 1
FIG. 3
FIG. 2

INTERMITTENT OXYGEN DELIVERY SYSTEM AND CANNULA

This is a continuation of co-pending application Ser. No. 07/104,771, filed on Oct. 5, 1987, now abandoned.

BACKGROUND OF THE INVENTION

The use of oxygen in respiratory therapy is fundamental and requires oxygen delivery at the location where the therapy is to be administered. Although oxygen is readily available at most institutions and hospitals in substantial quantity, for home care patients, oxygen is normally delivered in compressed oxygen cylinders on an "as needed" basis.

When compressed oxygen is used, it is withdrawn from a cylinder or other source via a regulator valve assembly at a prescribed and and definite flow rate. However, the user does not breathe all of the oxygen delivered; instead, less than half of the oxygen is actually inspired during the breathing cycle. As a result, a substantial amount of the oxygen is wasted and simply vented to atmosphere, obviously at a significant economic disadvantage.

To eliminate or reduce such a loss, a number of systems have been proposed including those described in U.S. Pat. No. 4,054,133 and referred to in "Chest", Vol. 74, July 1978, and U.S. Pat. Nos. 4,120,300, 4,278,110, and 4,381,002. The earliest patent refers to a pneumatic system incorporating a plurality of conduits, control chambers, and diaphragms for sensing pressure differences from a cannula during a user's respiratory cycle. The latter patents incorporate fluidic elements in combination with valves for controlling oxygen flow from a source.

SUMMARY OF THE INVENTION

The intermittent oxygen delivery system of the present invention incorporates state-of-the-art electronic components for sensing pressure differences during a user's breathing cycle and processing those signals in a unique manner for achieving the intended results. The advantages of the system of the present invention over prior art devices will be evident to those skilled in the art.

BRIEF DESCRIPTION OF THE DRAWINGS

FIG. 1 illustrates a nasal cannula used with the system of the invention;

FIG. 2 is a sectional view of the nasal cannula of FIG. 1;

FIG. 3 is a top plan view of the nasal cannula;

DETAILED DESCRIPTION OF THE INVENTION

Figure 6:
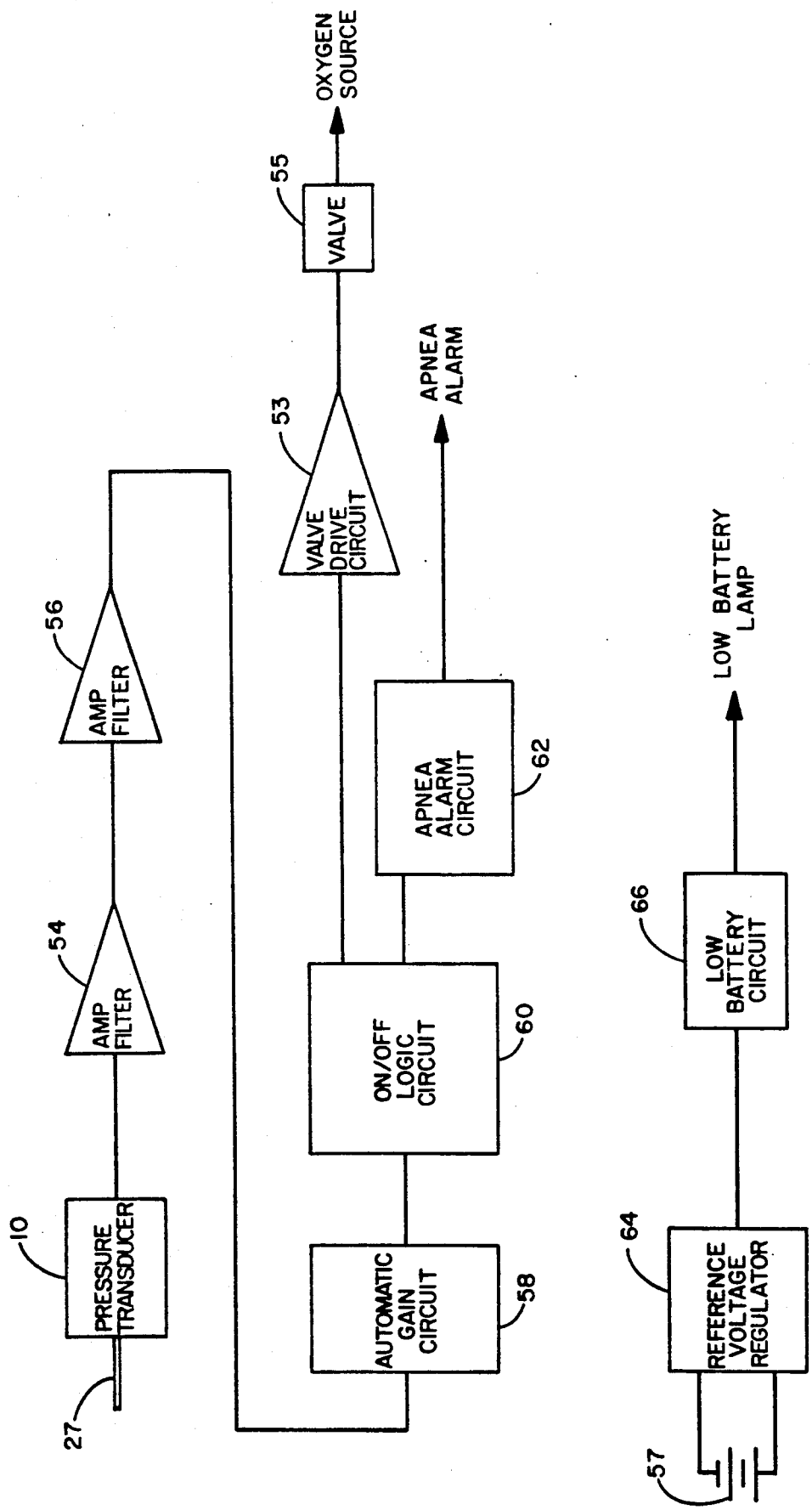
FIG. 6 is a block diagram illustrating the components of the system of the invention.
Figure 7:
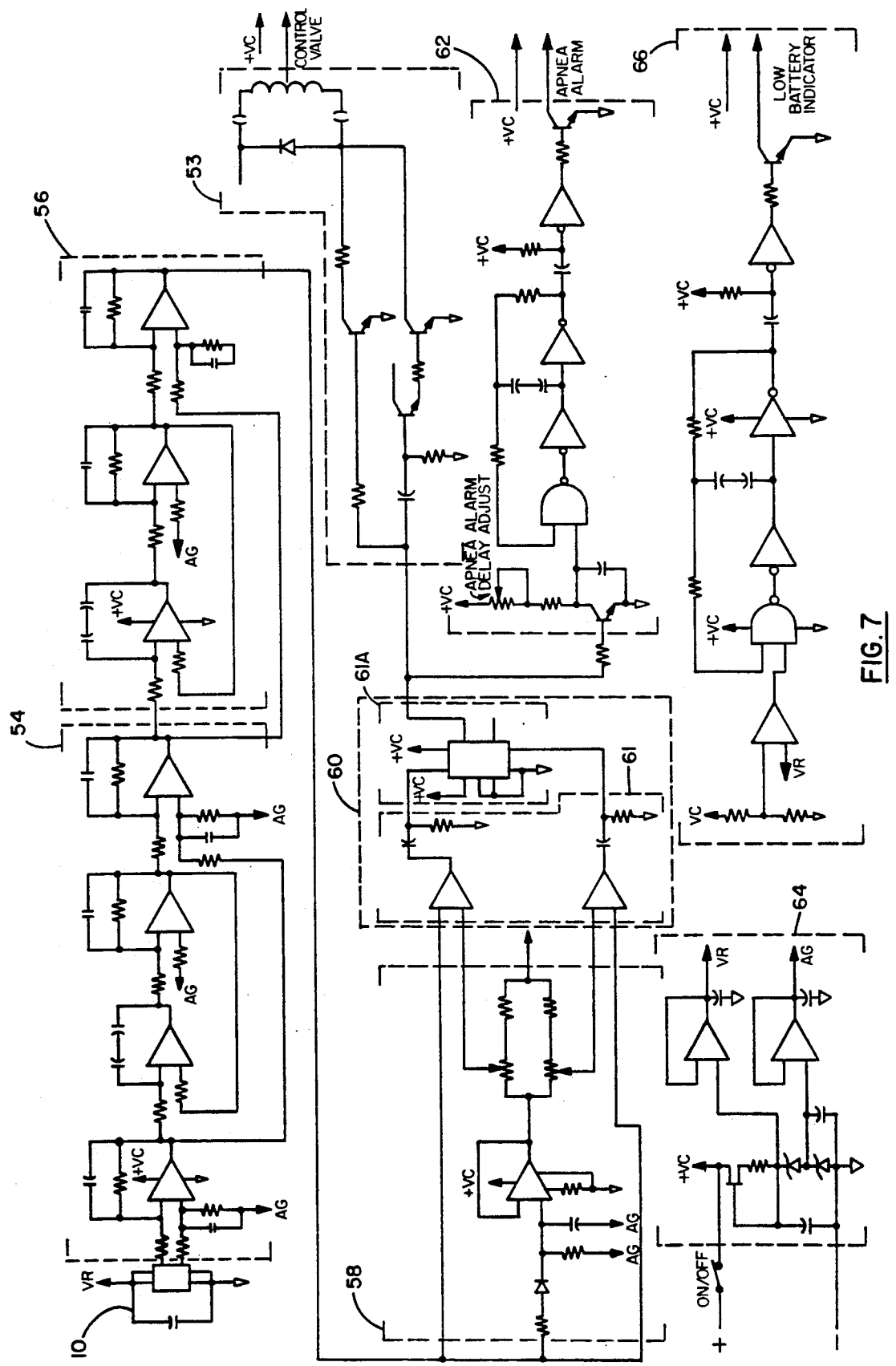
FIG. 7 is a detailed electronics schematic diagram of the electronics of the intermittent oxygen delivery system of the invention.

In FIGS. 1, 6 and 7 there is illustrated the system for intermittently delivering oxygen to a user, the delivery being controlled by the sensing system in response to the breathing cycle of the user. The system includes a pressure transducer 10 which senses breathing pressures via tubing 27 from a cannula or similar device secured to a patient, particularly the patient's nostrils. Such a cannula is provided with means for communicating gas pressures in response to the patient's breathing cycle the features and components of which will be more fully explained hereinafter. As the patient breathes, the entire pressure cycle including the positive and negative pressures are transmitted to the pressure transducer.

A significant advantage and advance of the system of the present invention is the ability to use a relatively inexpensive pressure transducer because of the manner of processing the signal from the transducer. More expensive pressure transducers which do not drift over a period of time could be used, but the cost of such transducers results in a system that is not economically advantageous. Because of the combination of components in applicant's system described herein, less expensive pressure transducers which may be used include silicon piezoresistive pressure sensors. These sensors commonly sense pressure from zero to 1.5 psi. Suitable examples of such sensors include Motorola sensor models MPX 10, MPX 11 and MPX 12, SenSym models SX01 and SX05, and Microswitch 170PC series sensors.

In the system of the invention the signal from the pressure transducer is received in sensing circuit 12 and processed through a series of amplifiers and band pass filters which condition and trim the transducer signal. In addition to trimming the frequency of the sensor signal, the amplifier components amplify the signal to at least 10,000 times the original signal strength, and preferably to a gain of about 50,000 to even about 100,000 times the original signal strength. Because the amplification of the signal from a relatively inexpensive transducer of the type mentioned above results in excessive noise, the signal is treated by band pass filter components of the amp-filters 54 and 56. These filters reduce the noise of the signal so that it is operationally useful and also trim the signal to correct the lowest negative pressure sensed by the pressure transducer to zero inspiratory pressure or zero pressure. More specifically, the signal is treated so that at the end of the breathing cycle between inspiration and expiration, that point in the breathing curve is always processed so that it corresponds to zero pressure. By so treating the signal, each breathing cycle is processed to a specific signal characteristic which is repeated accurately by the filtering system regardless of the actual drift or noise caused by the pressure transducer itself. Such a processing of the signal gives a continuing and accurate reproduction of the breathing pressure cycle notwithstanding drift or other inaccuracy of the pressure transducer component of the system.

The signal amplification and filtering steps are preferably carried out in stages, with specific components for that purpose shown in FIG. 7. In such a system, it may be preferred to amplify the signal, for example, to 100 times its original strength in the first stage, trim the signal, and in the second stage increase the amplification another 100 to 1000 times thereby yielding a total signal gain of between about 10,000 to 100,000 times the original strength. In this signal amplification stage of the system, if the signal is not sufficiently amplified, it will not yield the desired sensitivity for determining the on-off cycling in response to the user's breathing cycle pressures. On the other hand, if the signal is amplified too much, it may be too sensitive resulting in premature or inaccurate on-off cycling. The preferred amplification range described above will yield pressure sensitivity of about 0.1 cm $H_2O$ or less, quite adequate for the system of the invention. The signal is also trimmed in the second amplification filtering stage by a band pass filter component.

The amplified and filtered signal is then directed to automatic gain circuit 58 where it is further refined for removal of fluctuations. Normally, different users have different breathing cycle patterns. Even the breathing pattern of a single user will vary from time to time. In order to optimize the oxygen saving feature of the system of the invention, it is desirable to shut off the oxygen flow no later than the peak of negative inspiratory pressure, and preferably prior to that point of maximum negative pressure. It will be understood that oxygen delivered at the peak of inspiration will not be inspired to any significant extent. Such a fact is appreciated when considering the distance the oxygen must travel from the source, through tubing and delivery cannula, and from there through the patient's nostrils and airway, before it even reaches the lungs. In order for the logic circuit to accurately sense the cut off point for different breathing cycle patterns it is necessary to create uniform pattern cycles, which function is carried out by the automatic gain circuit (AGC). Specifically, the AGC circuit increases weak signals, for example, from a user who is breathing very lightly resulting in relatively weak signal strength. Similarly, overly strong signals are also normalized by the AGC circuit. Thus, all breathing pressure signals processed through the automatic gain control circuit fall within a preselected range without requiring separate calibration for each user.

From the AGC circuit the signal is passed to on/off-logic component 60. This component comprises two circuits, an on/off, dual threshold detector circuit 61, and a logic circuit 61A shown in FIG. 7. The on/off circuit detects the signal from the automatic gain control and at predetermined points of the breathing cycle representing selected breathing pressures, signals an on or off condition for switching an oxygen supply valve. Specific preferred preselected points are described hereinafter relating to FIG. 8. The points on the breath cycle pressure sensed by the on/off circuit at which the respective on and off signals are generated by the circuit are selected and provided in the circuit design. The logic circuit of the component holds the switch for the oxygen control valve in the then existing on or off condition until the next signal is generated by the on/off circuit. The logic circuit receives the successive on and off signals directly from the on/off circuit as seen in FIG. 7.

In FIGS. 6 and 7 valve drive circuit 53 is shown which is actuated by the signals from the on/off logic circuit 60 and which drive circuit causes valve 55 to be turned on and off in response to the pulse signals. The valve opens and closes a conduit to direct oxygen from an oxygen source such as a canister or cylinder 16 (FIG. 1), to the user via a pressure regulator or flow valve (not shown), an oxygen delivery tube 37, tubes 25 and 26, and nasal cannula 20. A preferred valve drive circuit comprises a pulse power circuit 53 illustrated in FIG. 7. In order to drive or operate a regulator valve of the type normally used to deliver oxygen from an oxygen source as described hereinabove, a relatively large amount of electrical energy is needed to initially open the valve as compared to the energy required to maintain the valve in an open condition. A larger amount of current for initially opening the valve is needed to pull the valve away from the valve seat, the valve normally being urged to a closed condition by a spring or similar biasing means. Once the valve is opened, the amount of energy required to maintain the spring in the open condition is substantially reduced. For this purpose, in this preferred embodiment shown in FIG. 7, pulse power circuit 51 provides a substantially greater current for a preselected time to open the valve, for example, approximately 10 milliseconds, and thereafter reduces the current to just enough energy required to maintain the valve in an open condition. Commonly, the amount of current used to maintain the valve in the open condition is in the order of $\frac{1}{4}$ to even 1/5 or less of the original current required to open the valve.

In another preferred embodiment, the system of the invention includes an apnea alarm circuit 62 for sensing interruption or termination of the breathing cycle of a patient or user. Such a circuit includes a timer and a delay function to create a signal for energizing an apnea alarm when no breathing cycle is sensed after a preselected time period. The apnea alarm circuit is connected to the on/off logic circuit 60. The apnea alarm circuit may also be provided with means for adjusting a time delay period before the alarm circuit is energized.

Additional components of the apparatus include a battery 57 for energizing the system, reference voltage regulator 64 for creating a steady reference voltage for driving the apparatus, and a low battery circuit 66 combined with a low battery lamp or other means for signaling when the battery is at a low condition and needs replacement. Such circuits are well known to those skilled in the art.

A most important feature of the system of the present invention is to deliver to a patient that amount of oxygen approximating, as closely as possible, the same amount of oxygen actually inspired by the patient during the breathing cycle. A significant problem of such accurate oxygen delivery based on patient use is that not only does the patient's breathing cycle vary from one part of the day to the other, i.e., between sleep and waking hours, but that the cycle itself may change rapidly, especially during the waking hours, depending on whether the patient is eating, resting, talking, etc. The cycle further fluctuates to due to patient anxiety or changes in rapidity of or depth of the breath which may occur from time to time due to physical or emotional influences. Obviously, these changes in breathing cycle patterns will substantially change the amount of oxygen needed by the patient to obtain maximum benefit from respiratory therapy in which oxygen is dispensed to the patient as part of the therapy.

Figure 8:
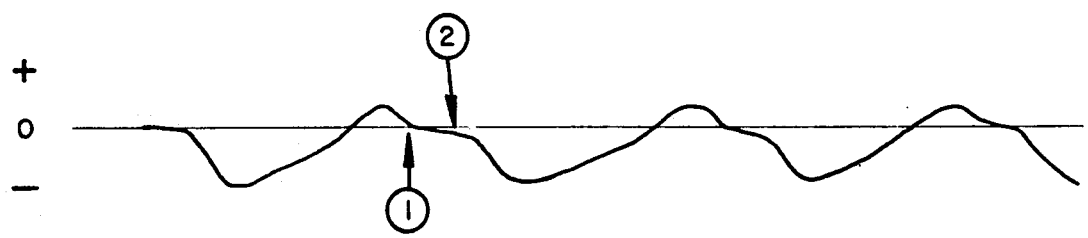
FIG. 8 is a graph illustrating a typical breathing pressure pattern and showing points on the pattern for operating the system.
Figure 8:
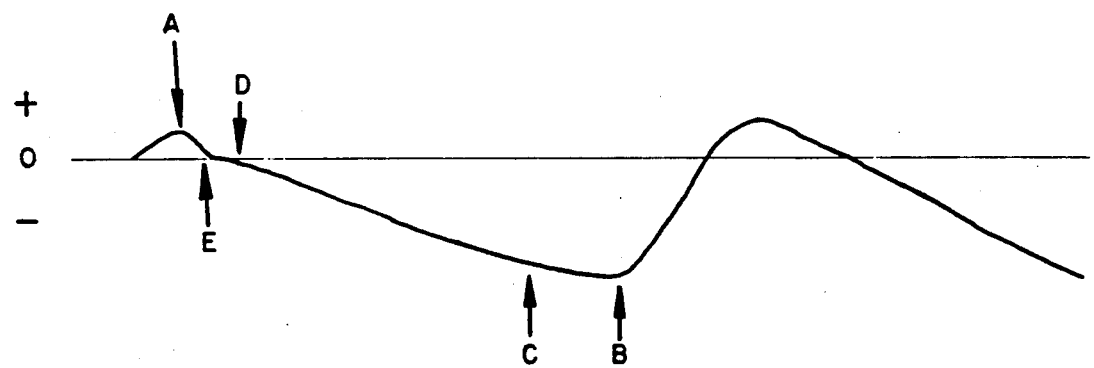

In FIG. 8 there is illustrated a typical breathing pressure cycle in which exhalation ends and inspiration begins at point A with negative pressure increasing to point B at which exhalation begins, with the curve being shown relative to positive and negative pressure. Assuming the patient's breath pattern to be regular, oxygen delivery could be turned on at point A where inspiration begins and turned off at point B where inspiration ceases and expiration begins. However, because only a relatively small amount of oxygen is actually inspired near the end of the inspiration cycle, to improve the efficiency of delivered oxygen used by the patient, it will be preferred to turn off the oxygen delivery prior to the end of inspiration at some earlier point, which eliminates or significantly reduces oxygen delivery to anatomical or physiological dead space, for example point C as shown in FIG. 8. As for the turn on, oxygen flow could be initiated at point D where negative pressure is first sensed by the system. Point A would usually not be a suitable turn on because from there to point D, there is still positive pressure in the airway system although it is decreasing. Moreover, because there is a substantial amount of tubing between the oxygen source and the patient, as well as the patient's airway between the nostrils and the lungs which must be filled with oxygen from the oxygen source even after the oxygen is turned on and the patient begins to inspire, there will be a significant time delay between the time the oxygen is initiated until it is received in the patient's lungs. Thus, it is desirable and preferred to initiate the oxygen delivery at some time prior to the beginning of inspiration, i.e., before the normal negative pressure turn on position D shown in the breathing cycle graph so that the dead space gas which is contained in the nasapharyngeal area, may be charged with 100% oxygen. Such a preferred position is represented as point E, the specific point being selected after taking into account the actual delay between turn on and delivery of oxygen to the patient's lungs due to the aforesaid factors.

The preferred turn on and turn off positions as illustrated in FIG. 8 may be accomplished by using pressure points in the breathing cycle, these pressures being preselected in the system circuitry. Alternatively, the system may utilize a time sequence during the breathing cycle for turning the oxygen flow on and off, it again being understood that the patient's breathing cycle will be normalized by the automatic gain control circuit in a manner as previously described.

In a preferred embodiment, the system may incorporate a microprocessor for enhancing the efficiency of the system. For example, such a microprocessor may be programmed to measure the actual volume of inspired gas within the breathing curve thereby avoiding pressure or time inaccuracies for turning on and off an oxygen delivery valve. Other advantages include programming the microprocessor to act as a second filter, as an automatic gain control circuit, to function as apnea monitor, and as a low battery test circuit. The microprocessor itself could also initiate the on and off signals as well as function as the threshold detector circuit as previously described. Any increased costs in utilizing such a microprocessor would be offset by eliminating the circuits which functions are carried out by the microprocessor.

The system of the present invention is used with a device for delivering oxygen to a patient and having means for communicating negative pressure during a patient's breathing cycle to the pressure transducer of the system. One such device is illustrated in FIGS. 1-3 comprising a nasal cannula 20 having an elongated hollow tubular cannula body 21 with a pair of gas inlet ports 42 and 44 at opposite ends of the body. These ports are connected to oxygen delivery tubes 25 and 26 (FIG. 1) which join main oxygen delivery tube 37. The cannula includes a pair of nasal tubes 22 and 24 for delivering oxygen to the nostrils of a patient when the device is secured with the nasal tubes in the patient's nares, the elongated tubular cannula body normally resting on the patient's upper lip. Oxygen is delivered through the nasal tubes via conduits 34 present in each of the nasal tubes and communicating with the hollow interior of the nasal cannula body.

The nasal cannula of the invention is provided with a unique configuration for communicating the pressure of the user's breathing cycle to the pressure transducer independent of the oxygen delivery components. More specifically, the nasal tubes 22 and 24 are provided with an interior wall 32 which extends across the interior surface of the nasal tube to form a pressure sensing conduit comprising an interior passageway 33 having a first opening at the outlet port 41 of the nasal tube and a pressure sensing port 36 adjacent cannula body 21. Thus, the pressure sensing conduit is separate from and independent of the oxygen delivery conduit system of the cannula. Relatively small diameter tubes 28 are secured to the pressure sensing ports 36 which tubes meet at union 29 connected to tubing 27 for communicating the breathing pressures to pressure transducer 10. By incorporating such features, the pressure-directing conduit 33 including pressure sensing port 36 are independent of the main cannula body interior and do not interfere or enter the interior of the cannula body 21. Thus, the pressure communicating tubing can be secured and repaired independently of the nasal cannula body without interfering with or taking up space in the gas delivery tubing 25 and 26. When the cannula is secured on a user or patient, as the patient breathes through his or her nostrils, gas pressure created during the breathing cycle is communicated through conduit 33, tubing 28 and 27 to the pressure transducer 10 thereby setting up the signal which is processed through the system in a manner as described hereinabove.

Figure 4:
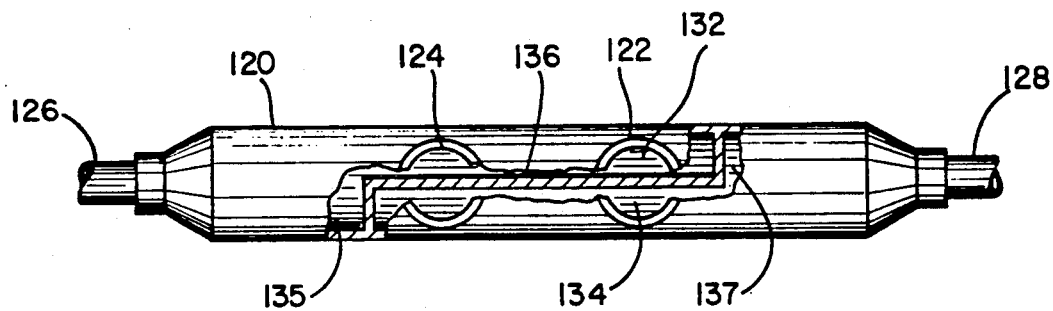
FIG. 4 is a top view, partially cut away, showing another nasal cannula embodiment used with the system of the invention.
Figure 5:
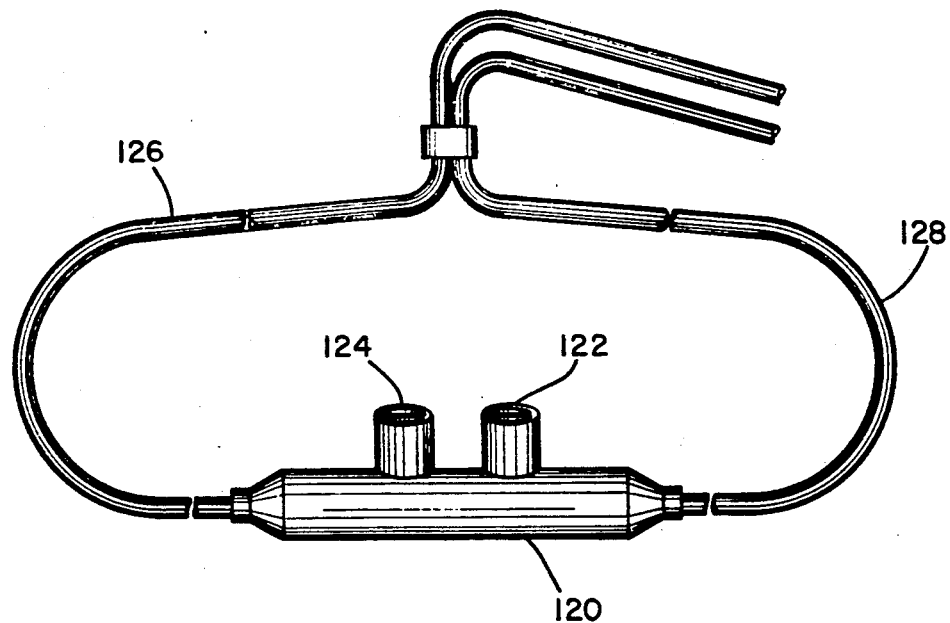
FIG. 5 is a side view of the cannula of FIG. 4 with attached tubing.

Another nasal cannula embodiment useful in the system of the invention is shown in FIGS. 4 and 5. In FIG. 4, the nasal cannula 120 is partially cut away to expose a wall or barrier 136 formed along the interior of the otherwise hollow elongated tubular cannula body. Wall 136 extends from the bottom to the top interior surface of the cannula body to form two separate chambers 135 and 137. The specific shape of wall 136 is not so important so long as it serves the function of forming the two chambers interiorly of the cannula body and which chambers are air-tight so that there is no leakage of air or pressure venting between the chambers. Wall 136 also extends upwardly through the two nares or nasal tubes 122 and 124 thereby also forming separate passageways 132 and 134 therein. Accordingly, each separate passageway in the nares or nasal tubes communicate with one of the interior cannula chambers. In the cannula shown in FIG. 4, passageway 132 communicates with interior chamber 135 and passageway 134 communicates with interior chamber 137.

As also shown in FIG. 5, cannula 120 is connected with separate gas supply tubing 126 and 128 which lead to different components of the system of the invention. Tube 126 connected at one end of the cannula body is for supplying oxygen to the cannula and thus is connected to oxygen supply valve or regulator control valve 14 shown in FIG. 1. Oxygen supply tubing 128 connected at the opposite end of the nasal cannula 120 is connected to pressure transducer 10 (FIG. 1) thereby communicating breathing pressures thereto for operating the sensing circuit 12 of the invention as previously described. Thus, since the nasal cannula shown in FIGS. 4 and 5 is formed into two chambers, each nasal tube 122 and 124 will be used both for delivering oxygen to the user from the oxygen source via tube 126 and for sensing the user's breathing pressure in the breathing cycle via passageway 134, chamber 137 and tubing 128 to operate the oxygen control delivery system of the invention.

I claim:

1. A nasal cannula comprising:
an elongated hollow tubular cannula body having a single port at each opposite end thereof, each port for being attached to or receiving a single tube, respectively, and
a single pair of nasal tubes integral with and extending from said cannula body, each of said nasal tubes having a first port at an end thereof and a second port on an exterior sidewall thereof, and an internal divider wall extending across the interior of each of said nasal tubes and defining a first passageway extending between the hollow cannula body and said first port and a second passageway extending between said first port and said second port.

2. A nasal cannula comprising:
an elongated tubular cannula body having a gas supply port at a first end thereof and a pressure sensing port at a second end thereof,
a pair of nasal tubes extending from said cannula body and having an outlet port at the end thereof opposite said cannula body, and
a wall member secured in said cannula body and forming a first and a second chamber therein, said wall member extending into each nasal tube to form a first and a second passageway therein, wherein said first chamber is in communication with said first passageway and said second chamber is in communication with said second passageway.

* * * * *